United States Patent [19]

Grosse et al.

[11] Patent Number: 5,573,536

[45] Date of Patent: Nov. 12, 1996

[54] LOCKING NAIL FOR TREATING FEMORAL FRACTURES

[75] Inventors: Arsène J. Grosse, Strassbourg, France; Hans E. Harder, Probsteierhagen, Germany

[73] Assignee: Howmedica GmbH, Schoenkirchen, Germany

[21] Appl. No.: 486,154

[22] Filed: Jun. 7, 1995

Related U.S. Application Data

[63] Continuation of Ser. No. 153,831, Nov. 17, 1993, abandoned, which is a continuation of Ser. No. 926,086, Aug. 6, 1992, abandoned.

[30] Foreign Application Priority Data

Aug. 9, 1991 [DE] Germany .............................. 9109883 U

[51] Int. Cl.$^6$ ...................................................... A61B 17/56
[52] U.S. Cl. ...................................................... 606/60; 606/67
[58] Field of Search .................................. 606/62–68, 72, 606/73

[56] References Cited

U.S. PATENT DOCUMENTS

| | | | |
|---|---|---|---|
| 3,433,220 | 3/1969 | Zickel . | |
| 4,475,545 | 10/1984 | Ender | 606/64 |
| 4,622,959 | 11/1986 | Marcus | 606/64 |
| 4,667,664 | 5/1987 | Taylor | 606/64 |
| 4,697,585 | 10/1987 | Williams | 606/64 |
| 4,805,607 | 2/1989 | Engelhardt | 606/64 |
| 4,827,917 | 5/1989 | Brumfield . | |
| 4,858,602 | 8/1989 | Seidel | 606/64 |
| 4,875,475 | 10/1989 | Comte | 606/64 |
| 4,877,019 | 10/1989 | Vives | 606/64 |
| 4,913,137 | 4/1990 | Azer | 606/64 |
| 4,976,258 | 12/1990 | Richter | 606/64 |
| 5,122,141 | 6/1992 | Simpson | 606/64 |
| 5,176,681 | 1/1993 | Lawes | 606/64 |

FOREIGN PATENT DOCUMENTS

| | | |
|---|---|---|
| 0257118 | 7/1986 | European Pat. Off. . |
| 0192840 | 9/1986 | European Pat. Off. . |
| 0226701 | 7/1987 | European Pat. Off. . |
| 0306709 | 3/1989 | European Pat. Off. . |
| 0355411 | 2/1990 | European Pat. Off. . |
| 2387637 | 11/1978 | France . |
| 1248228 | 8/1967 | Germany . |
| 4012995 | 10/1990 | Germany . |
| 9101035 | 4/1991 | Germany . |
| 9102018 | 5/1991 | Germany . |
| 2209947 | 9/1987 | United Kingdom . |
| 2209947 | 6/1989 | United Kingdom . |
| 2209947 | 6/1989 | United Kingdom . |
| 8907056 | 8/1989 | WIPO . |

OTHER PUBLICATIONS

Plus German Search Report for G 91 09 883.1 (dated Jul. 6, 1992) plus EPO Search Report for EP 93 10 0439 dated Jul. 20, 1993.

European Search Reported dated Nov. 24, 1992.

*Primary Examiner*—Michael A. Brown
*Attorney, Agent, or Firm*—Peter C. Richardson; Lawrence C. Akers; Elizabeth O. Slade

[57] ABSTRACT

A locking nail for treating femoral fractures has a generally cylindrical proximal portion to be positioned in the medullary canal. The proximal portion has an oblique bore for positioning and guiding a femoral neck screw. The nail has a distal portion provided with at least one cross bore for receiving a bone screw. The distal portion has an annular cross-sectional profile including an axial slot. The annular profile may be in the form of a clover leaf. A transition portion of said nail is located between the proximal and distal nail portions. The longitudinal slot extends from the transition portion to the distal tip of the distal portion.

6 Claims, 2 Drawing Sheets

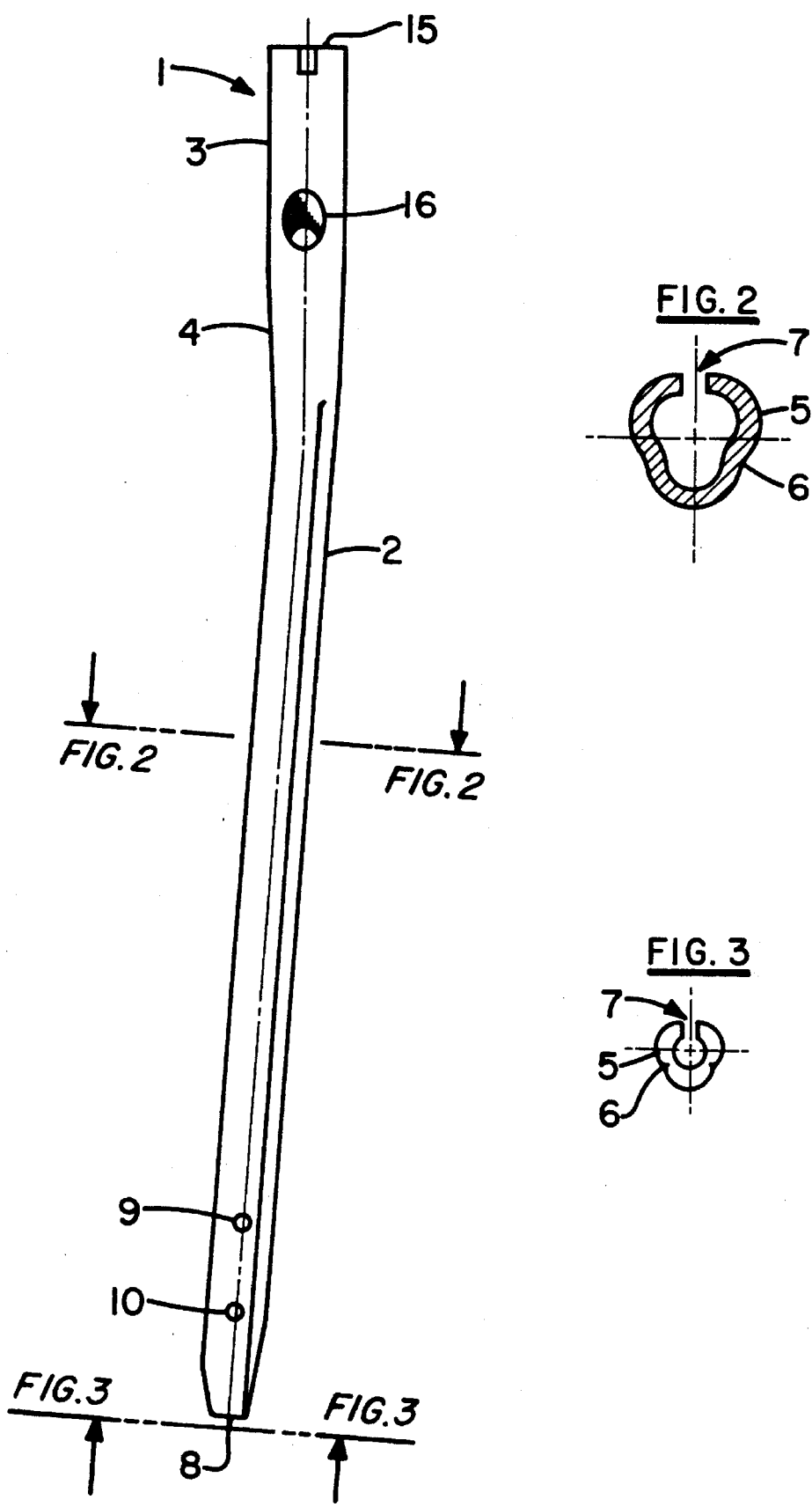

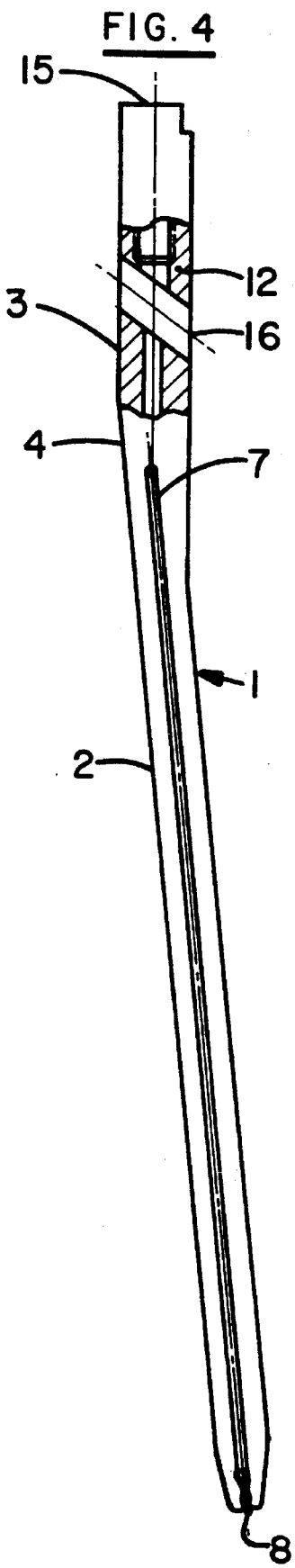
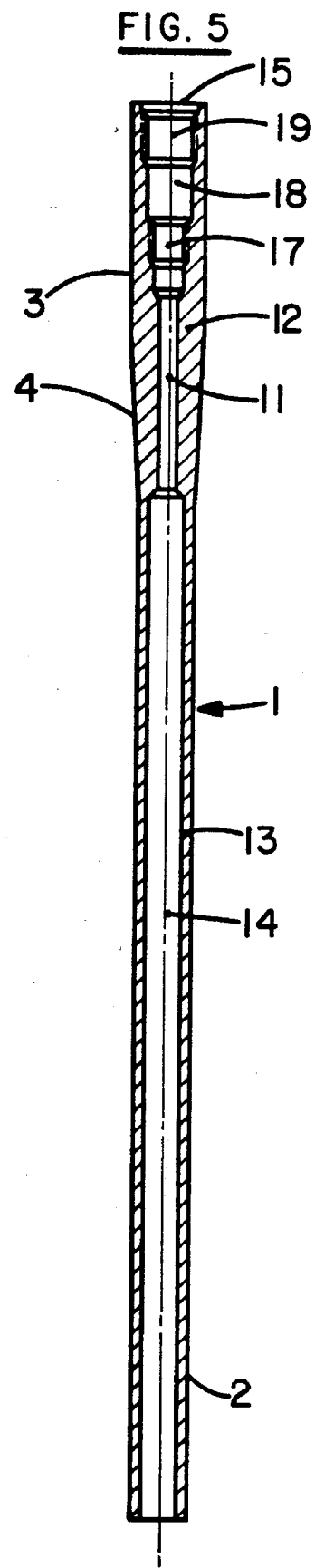

LOCKING NAIL FOR TREATING FEMORAL FRACTURES

This is a continuation of application Ser. No. 08/153,831, filed on Nov. 17, 1993, now abandoned, which is a continuation of application Ser. No. 07/926,086, filed on Aug. 6, 1992, now abandoned.

BACKGROUND OF THE INVENTION

1. Field of the Invention

The present invention relates to a locking nail for treating femoral fractures in the medium and trochanter region. More particularly, the invention relates to a locking nail having a closed first section and an open second section containing longitudinal slot.

2. Description of the Prior Art

An osthesynthesis device to be used for sub-trochanter fractures is disclosed in European Patent 0 257 118, which device comprises a closed locking nail including an oblique bore for guiding and positioning a femoral neck screw in the proximal portion thereof. Since the locking nail, known as well as the "Gamma Nail" (shown in copending U.S. Ser. No. 281,730, filed Dec. 9, 1988), is not used itself for treating fractures of the femur neck, the nail is shorter than usual, merely including cross bores in its distal portion to fix the nail in an axial and rotational direction. A nail having a varying radius through its cross-section is shown in U.S. Pat. No. 4,976,258, which issued to the assignee of the present invention.

The femur neck screw fits in the oblique bore and is thus effectively secured against pivoting in the plane clamped thereby and about an axis defined by the locking nail. To rotatably secure the femur neck screw a rotational lock, for example, a locking pin is provided. This rotational lock allows the femur neck screw to axially move so that the screw may yield when the bone shortens during healing.

While the known locking nail according to European Patent 0 257 118 has a closed profile, the so-called Küntscher Nail has an open clover leaf profile having a longitudinally extending slot. The strength of the mechanical attachment in the marrow space or medullary canal, in particular the rotational stability of the Küntscher Nail, can be improved by use of the present invention.

An advantage of a slotted nail is seen in its elasticity resulting from the axial longitudinal slot so that a certain spring effect is obtained, and as the nail is hammered in, it is laterally pressed against the bone material.

The nails referred to are used in the treatment of fractures in the central third or, respectively in the sub-trochanteric region. However, these nails are less suited for the treatment of complicated femoral fractures.

SUMMARY OF THE INVENTION

It is the object of the present invention to provide a locking nail which is safely fixed in the femur and which is suited to be used in the treatment of complicated femoral fractures in the central and trochanter region.

These and other objects are achieved by a locking nail according to the invention which comprises an open clover leaf profile including an axial longitudinal slot in the distal nail portion as well as at least a cross bore for receiving a bone screw. The longitudinal slot extends substantially from the free distal nail end to the transition portion joining the distal nail portion and a cylindrically closed proximal portion. The proximal portion may be provided with an oblique bore to hold and guide a femoral neck screw. The clover leaf shaped distal portion has a smaller diameter than the cylindrical closed proximal portion, wherein the transition portion may be formed conically.

According to an embodiment of the invention, the distal nail portion is disposed under an angle of 4° to 7° in the anterior-posterior plane with respect to the proximal nail portion. In addition, the distal nail portion may be disposed under an angle of 6° to 10° in the lateral-medial plane with respect to the proximal nail portion.

According to a further embodiment of the invention, an internal thread is provided above the oblique bore to receive a locking pin. A second internal thread may be formed at the proximal nail end to receive an insertion aid such as a targeting device or a hammer.

The locking nail according to the invention, the length of which may be 240 to 480 mm, is particularly suited in the treatment of complicated femoral fractures, wherein it provides for a high mechanical holding force in the marrow space and a high security against rotation. Due to the longitudinal slot, a certain elasticity of the nail is obtained. By means of the cross bores provided in the lower distal region, the nail is fixed by bone screws in an axial and rotational direction. The locking nail according to the invention may be bent to conform to the physiological antecurvation of the femur. The femur neck screw may be positioned in the oblique bore and secured against rotation by a locking pin which is inserted in the proximal end of the nail and fixed in the internal thread, wherein an axial motion of the nail is still allowed. A beating tool for operating the locking nail or a target device to determine the position of the oblique bore when the femur is drilled laterally to insert the femoral neck screw, may be fixed in a second internal thread provided at the distal nail end.

The nail according to the invention is formed from a cylindrical solid tube made of a non-corrosive, physically compatible material such as cobalt chrome, titanium or stainless steel. The tube is internally drilled, wherein the internal bore preferably has a larger diameter in the distal nail portion than in the proximal nail portion, and in a second step, the axial longitudinal slot is formed. Thereafter the outer periphery of the tube is worked to form the clover leaf shaped distal portion having a smaller diameter than the proximal portion and the tapered transition portion and the cylindrical proximal portion. The cross bores and internal threads are formed as known per se. The clover leaf profile is formed by a press-forming step.

While several examples of the present invention have been described, it is obvious that many changes and modifications may be made thereunto, without departing from the spirit and scope of the invention.

BRIEF DESCRIPTION OF THE DRAWINGS

In the drawings, wherein similar reference characters denote similar elements throughout the several views:

FIG. 1 is a side view of a locking nail according to the invention of treating fractures in the right femur along the anterior-posterior plane;

FIG. 2 is a section through the nail of FIG. 1 taken along the line A—A;

FIG. 3 is an end view of the nail of FIG. 1 along the lines B—B;

FIG. 4 is a front view partially in cross-section of the nail of FIG. 1; and

FIG. 5 is a cross-sectional view of the nail of the locking nail of FIG. 1.

DESCRIPTION OF THE PREFERRED EMBODIMENT

Referring to FIGS. 1–5 there is shown a locking nail 1 which includes a distal portion 2, a proximal portion 3 and a tapered transition portion 4. The cross section of distal portion 2 shown in FIGS. 2 and 3 is formed like a trifoliate open clover leaf including elevations 5 and depressions 6. An axial longitudinal slot 7 extends from the free distal nail end 8 across the total length of the distal portion 2 to define the open clover leaf profile. The lower range of the distal portion 2 is provided with a pair of cross bores 9 and 10.

Proximal portion 3 is in the form of a closed cylinder. The cross-section of the proximal portion 3 is circular, having a larger diameter than that of the distal portion 2. The wall thickness 12 in the proximal portion 3 of the locking nail 2 is relatively large with respect to its inner bore 11, whereas the distal wall thickness 13 is rather small when compared with the inner bore 14 of the distal portion. The inner bore 11 extends from the end to the distal portion up to the free proximal nail end 15.

As seen in FIG. 4, an oblique bore 16 for guiding and positioning a screw for the neck of the femur (not shown) is placed proximally of transition portion 4 in proximal portion 3. Proximal portion 3 is provided with a threaded internal bore 17 as shown in FIG. 5 to receive a locking pin (not shown). Adjacent the internal thread 17 the inner bore 11 is cylindrically enlarged up to the proximal nail end 15. The cylindrical enlarging portion 18 and a second internal thread 19 adjacent the proximal end 15 are used for receiving and positioning a target device or a hammer.

By bending the transition portion 4, the straight distal portion 2 in the medial-lateral (M-L) plane is positioned under an angle of approximately 6°–10° with respect to an M-L plane containing the axis of closed cylindrical proximal portion 3 (FIG. 4). The distal portion may also be angled in the anterior-posterior plane under an angle of approximately 4°–7° (FIG. 1) with respect to the anterior-posterior plane of the proximal portion 3.

The transition portion 4 may be partly conical in shape increasing in diameter on moving proximally form distal portion 2 to proximal portion 3.

We claim:

1. A tubular locking nail extending along a longitudinal axis for treating femoral fractures in the medium and trochanter region comprising:

(a) a proximal portion having a closed generally cylindrical shape generally concentric with said longitudinal axis to be positioned in the femur marrow space, said proximal portion having an oblique bore for positioning and guiding a femoral neck screw and having a diameter D and (b) a distal nail portion with at least one cross bore for receiving a bone screw, said distal nail portion having an annular cross-section with a diameter d and including an axial longitudinal slot resulting in an open distal nail portion profile, and (c) a transition portion located between said proximal portion and said distal portion, said transition portion tapering continuously from said diameter D to said diameter d, wherein said diameter D is larger than said diameter d and wherein said axial longitudinal slot in said distal portion extends substantially from said transition portion to a tip of said distal portion.

2. The locking nail of claim 1 wherein the distal nail portion is disposed in the medial-lateral plane of the locking nail under an angle of between 6° and 10° with respect to a medial-lateral plane containing the axis of the proximal nail portion.

3. The locking nail of claim 2 wherein the distal nail portion is disposed in the anterior-posterior plane of the locking nail under an angle of between 4° and 7° with respect to the proximal nail portion.

4. The locking nail of claim 3 wherein the proximal nail portion has a threaded internal bore.

5. The locking nail of claim 4 wherein a second internal thread for receiving an insertion aid is formed adjacent the proximal nail end.

6. The locking nail of claim 1 wherein said annular cross-section has an open clover leaf shape.

* * * * *